United States Patent
Hlavacek et al.

(10) Patent No.: US 7,300,625 B1
(45) Date of Patent: Nov. 27, 2007

(54) CHLORINE GAS GENERATING CANDLE

(75) Inventors: Vladimir Hlavacek, Clarence, NY (US); Carl Gotzmer, Accokeek, MD (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 499 days.

(21) Appl. No.: 10/807,584

(22) Filed: Mar. 18, 2004

(51) Int. Cl.
*A61L 2/20* (2006.01)

(52) U.S. Cl. ............... 422/33; 422/305; 422/306; 423/504; 252/187.1

(58) Field of Classification Search ............ 423/504; 252/187.1
See application file for complete search history.

(56) References Cited

U.S. PATENT DOCUMENTS

| | | | |
|---|---|---|---|
| 1,566,040 A * | 12/1925 | Partridge et al. ........... 423/506 |
| 4,316,874 A | 2/1982 | Kasama et al. ............. 422/126 |
| 4,687,640 A | 8/1987 | Schillaci .................... 422/120 |
| 4,981,655 A | 1/1991 | Kolbe et al. ............... 422/165 |
| 5,154,911 A * | 10/1992 | Benson et al. ............. 423/502 |
| RE36,199 E | 4/1999 | Zhang et al. ........... 252/187.31 |
| 6,030,583 A | 2/2000 | Kshirsagar et al. ........ 422/126 |
| 6,099,806 A * | 8/2000 | Cortellucci et al. ........ 422/126 |
| 6,231,816 B1 | 5/2001 | Zhang et al. ............... 422/126 |
| 6,264,896 B1 | 7/2001 | Zhang et al. ............... 422/126 |
| 2001/0030311 A1 | 10/2001 | Zhang et al. .......... 252/187.31 |

* cited by examiner

*Primary Examiner*—E. Leigh McKane
(74) *Attorney, Agent, or Firm*—Fredric J. Zimmerman

(57) ABSTRACT

A chlorine gas generating candle in a vented container which serves as a portable means to generate heated chlorine gas for killing insects, bacteria, viruses and other dangerous biological agents. The device has application in sanitizing dwellings, swimming pools and the like, and is effective in case of accidental release and/or biological attack. The chlorine gas generating candle disinfects an enclosed space with a quantity of heated chlorine gas. The chlorine gas generator is a self contained unit including an igniter which can be activated to initiate a self propagating burn of the entire candle and a resultant distribution of toxic chlorine gas. The use of one or a plurality of chlorine generators described in this application can provide any desired concentration of the killing gas. The chlorine gas generating candle can be safely and easily transported and does not require a source of power to operate.

12 Claims, 2 Drawing Sheets

CHLORINE GAS GENERATING CANDLE

STATEMENT OF GOVERNMENT INTEREST

The invention described herein may be manufactured and used by or for the Government of the United States of America for government purposes without the payment of any royalties therefor.

BACKGROUND OF THE INVENTION

1. Field of the Invention

The invention relates to the production of chlorine gas for the destruction of undesirable organisms by burning a candle which produces chlorine gas in a self propagating exothermic reaction.

2. Description of the Background

Chemicals having the capacity to disinfect and sanitize are widely used in applications as pesticides to eliminate existing organisms and as a preventative treatment to avoid growth or infestation of unwanted organisms. Chlorine is useful in many such applications because of the broad variety of organisms which can be killed by the introduction of chlorine into their environment. Chlorine can successfully destroy biological warfare agents, including viruses, such as equine encephalomyelitis; bacteria, such as those which cause plague, anthrax and tularemia; and fungi, such as coccidioidomycosis; as well as toxic products expressed by such microorganisms, for example, the botulism toxin expressed by the common *Clostridium botulinium* bacterium. Chlorine gas can be introduced to liquids such as water and it is often used in this fashion to disinfect swimming pools and to prevent the growth of algae in water cooled systems. Chlorine gas can be delivered to the atmosphere to disinfect a closed space by raising the concentration of chlorine, in the air, to a toxic level.

Chlorine is highly toxic, so its use in the form of the liquified gas (commonly sold in steel cylinders holding 75 pounds or more) presents a significant hazard. For this reason, chlorine is also sold in the form of a concentrated solution of sodium hypochlorite (NaOCl, sometimes called "liquid chlorine" or swimming pool bleach) or as the solid calcium hypochlorite (CaOCl.sub.2, "solid chlorine" or bleaching powder). These substances, which are quite costly relative to liquified chlorine gas, usually contain, respectively, excess sodium hydroxide or calcium oxide. Chlorine in this form is safe to handle but it is adapted for use by introducing it to a liquid.

Another alternative to the use of liquified chlorine gas is to generate chlorine on site by the electrolysis of a concentrated aqueous solution of sodium chloride (NaCl or salt) in a two-compartment electrolytic cell. The production of chlorine electrochemically in large chlorine/caustic plants using complex cells which keep the products from the anode separate from the products of the cathode is a well known art (see Kirk-Othmer's Encyclopedia of Chemical Technology, Third Edition, volume 1, pages 799-865 and volume 8, pages 662-695). Electrolysis is an effective way of producing chlorine gas but the aqueous solution must be prepared and a power source is required to initiate the necessary reaction.

A closed space can be disinfected or pests within the space can be eliminated by filling the space with a toxic gas for a period of time long enough to kill the insect. This method is effective for killing; however, this method generally requires several hours to be effective. Typical of these is the method disclosed by Forbes in the U.S. Pat. No. 4,817,329, in which insects, e.g., termites, are killed by applying a heated gas, such as heated air, to wooden surfaces until the building surfaces are heated to a temperature about 120° F. to 135° F. However, this method, using the described temperatures, is not effective for other organisms such as fungi, and toxic molds, bacteria and viruses. Additionally, this type of work must be done in remote locations where a power source is often not available. The availability of heated chlorine gas would enhance the effectiveness as to other organisms but known methods of generating chlorine gas are not conducive to use in a portable system. The bottled pressurized chlorine gas is dangerous to transport and the apparatus for producing chlorine by electrolysis is cumbersome and requires power.

There remains a need for a more portable means to generate heated chlorine gas, which can be safely and easily transported and which does not require a source of power to operate. A number of prior art patents employ solid chemical candles used to produce oxygen to be breathed in an emergency situation. These generally establish a self propagating exothermic reaction to generate the oxygen. Metal powder is the preferred fuel. Iron, manganese, cobalt, copper and nickel are disclosed as fuel, see Zhang, U.S. Pat. No. 6,264,896 and Kshirsagar, U.S. Pat. No. 6,030,583. Copper oxide and nickel oxides are disclosed as catalysts, see Zhang, U.S. Pat. No. 6,264,896. Chlorates and perchlorates of sodium, lithium and potassium are disclosed as sources of oxygen, see Zhang, U.S. Pat. No. 6,264,896. These prior art patents also vary the composition of layers of pyrotechnic material to alter the product and the rate of production. The concept of the solid chemical candle has advantages which are equally well-suited for generating chlorine gas in the present context. It would be greatly advantageous to adapt the existing concept to provide a solid chemical candle for the production of heated chlorine gas. This would provide a convenient and cost-effective device that can be conveniently stored and quickly carried to the location where it is most needed in case of germ warfare, terrorist attacks in areas that are difficult to reach, etc.

SUMMARY OF THE INVENTION

It is an object of the present invention to provide a process and an apparatus for generating heated chlorine gas from a solid chemical candle, which can be easily stored and transported and which does not require the mixing of any components.

It is another object of the present invention to provide a process and an apparatus for generating heated chlorine gas from a solid chemical candle for use in sanitizing dwellings, swimming pools and the like, and also for sanitizing accidental biological spills and/or biological attacks It is a further object of the present invention to provide a chlorine gas generating chemical candle which can be ignited by a self contained mechanism.

It is an additional object of the present invention to provide a chlorine gas generating chemical candle which will burn completely in a self propagating fashion after it has been ignited.

These and other objects are accomplished with a chlorine generation composition and portable apparatus for generating chlorine by exothermic reactions. The chlorine generation composition generally includes a fuel, a catalyst, a chlorine producing compound and an oxygen producing compound. Specifically, the chlorine generating composition is a metal chloride comprising a metal powder as a fuel; a catalyst selected from the group consisting of copper oxide, nickel oxide, or mixtures thereof; an additive for generating chlorine; and an oxygen source selected from the group consisting of alkali metal chlorates, alkali metal perchlorates, and mixtures thereof. The chlorine generating compound can optionally further include a binder. The chlorine generating composition is incorporated in a candle form with several layers having varied compositions. The candle has a generally cylindrical shape with a layer of fuel rich material, usually of a conical shape, that can guarantee a permanent propagation of the combustion zone. Since the reaction and oxidation of chlorides to elemental chlorine is only accompanied by small heat effects, it is necessary to have an energy providing layer to cause the self-propagation phenomena. An ignition layer is ignited by firing a primer, and heat from the ignition layer then ignites the reaction of the candle body, generating chlorine.

The chlorides generating chlorine are mixed with the oxygen producing salt either in a homogeneous way or certain sandwiches of heterogeneous mixtures can be produced. The reaction is started by an igniter that can be fired thermally or mechanically by a spring-actuated hammer against the primer. The candle is wrapped in a thermal insulating layer to avoid large heat losses from the hot surface that would result in an extinction of the candle. The entire assembly is placed in an appropriate housing that allows a rigid construction for the candle and that makes it possible for the generated chlorine to freely escape to the surroundings. To provide a rigid form of the candle, glass wool or wollastonite materials are used.

The gas produced by the burning candle contains both chlorine and oxygen and is highly suitable to all types of disinfection activity discussed above.

Typically, the enclosure or the closed space will be disinfected by the combination of gas produced by the candle described above with the supporting heat generator that can be produced electrically or chemically by an exothermic reaction. The enclosed space can be a building, barn, silo, storage room or a military bunker.

The use of one or a plurality of chlorine generators described in this application can provide any desired concentration of the killing gas. Different insects, bacteria, viruses and dangerous warfare agents require different temperatures for effective destruction. For example, anthrax requires a combination of high temperature and chlorine concentration.

DETAILED DESCRIPTION OF THE PREFERRED EMBODIMENT

Figure 1:
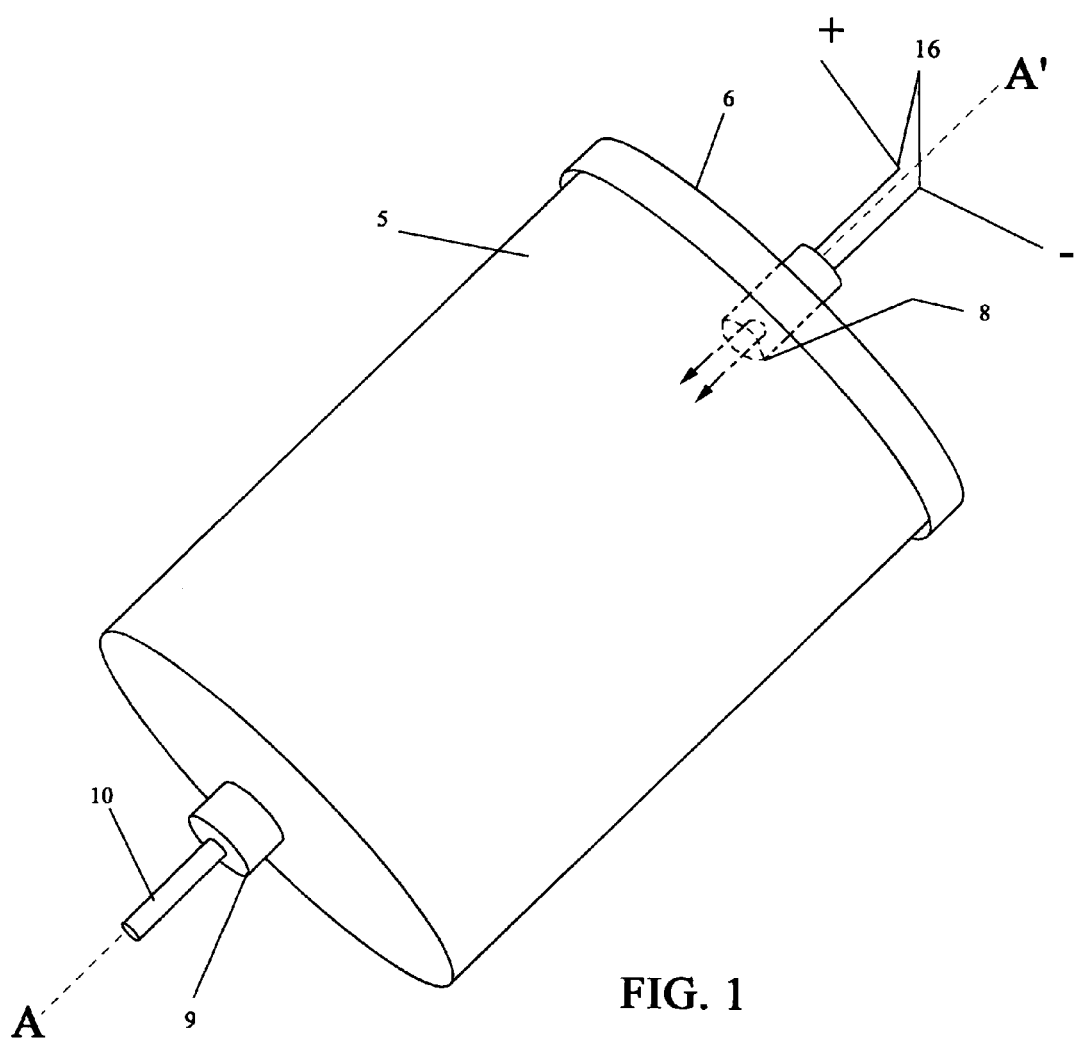
FIG. 1 is a perspective view of the chlorine gas generator of the present invention.

The present invention comprises a process and apparatus for producing chlorine gas. The apparatus 13 is a chemical candle 4 disposed within a container 5. The container 5, shown in FIG. 1, is constructed of rigid non-flammable material such as stainless steel, preferably of cylindrical shape and having an open end and a closed end. A cover lid 6 is provided to fit the open end of the container 5 and is equipped with one or more toggle latch(es) 7 or other closures for releasably closing the container 5 and forming an airtight seal. The cover lid 6 has an aperture for receiving a first stopper 8 which entirely occupies the aperture and maintains the airtight seal. The closed end of the container 5 is provided with an aperture for receiving a second stopper 9. Alternatively, the aperture, in the closed end, may be defined by an integral threaded flange extending inwardly or outwardly from the closed end and being formed to receive a mating threaded fitting thereon. The second stopper 9 supports and retains a discharge tube 10 that passes through the second stopper 9 and is in fluid communication with the inside of the container 5.

Figure 2:
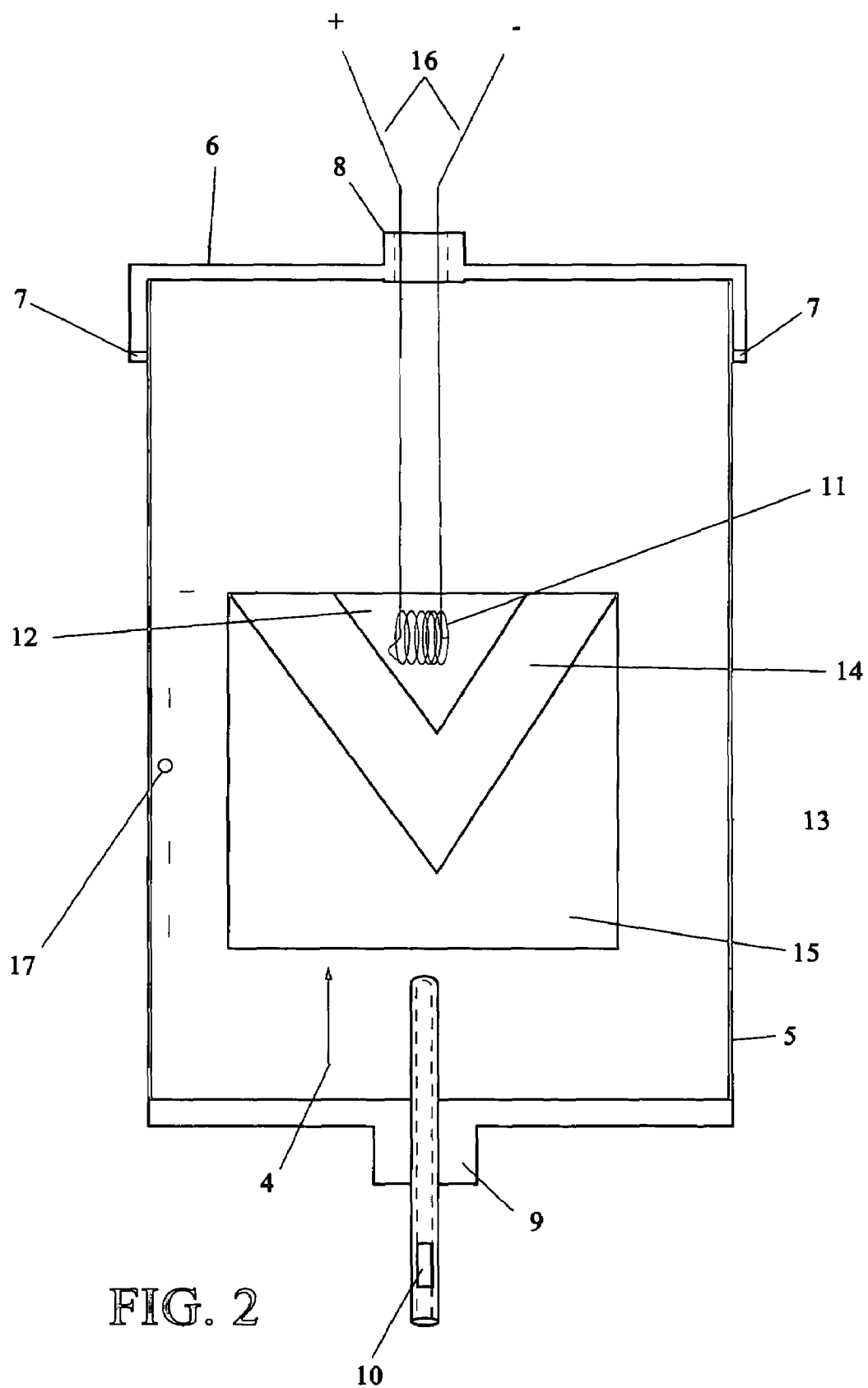
FIG. 2 is a cross-section view of the chlorine gas generator taken along the line A-A shown in FIG. 1.

The chemical candle 4 is disposed within the container 5 as shown in FIG. 2, and comprises a solid body formed of multiple segments. The chemical candle 4 is preferably of cylindrical shape and sized to fit centrally within the container 5 such that the chemical candle 4 and the inside surface of the container 5 are spaced apart by a distance of approximately 2 centimeters.

The chemical candle 4 includes an igniter 11, an ignition segment 12 and a chlorine generating segment.

The ignition segment 12 is preferably formed in an inverted conical shape with an opening at the base of the cone, into which the igniter 11 is disposed and fixed in place by suitable means, such as adhesive or a plug. In this configuration the ignition segment 12 is fired thermally by a pair of wires 16 connected to a coiled igniter 11, as shown in FIG. 2, the wires 16 passing out through the first stopper 8, to the outside of the container 5. As an alternative, ignition segment 12 may be fired mechanically by a spring-actuated hammer. Insulation material 17 is disposed inside the container filling the space between the chemical candle 4 and the inside surface of the container 5. The insulation material 17 may be, among others, carbon felt, glass wool, or wollastonite.

The chlorine generating segment further comprises a fuel rich layer 14, and a fuel lean layer 15 both having a chlorine generating composition (metal chloride comprising a metal powder as a fuel); a catalyst selected from the group consisting of copper oxide, nickel oxide, or mixtures thereof; an additive for generating chlorine; and an oxygen source selected from the group consisting of alkali metal chlorates, alkali metal perchlorates, and mixtures thereof. The chlorine generating segment can optionally further include a binder. The fuel rich layer 14 is also formed in an inverted conical shape conforming to that of ignition segment 12, and may be integrally molded in contact with the ignition segment 12. The fuel lean layer 15 is also likewise preferably formed in a conical shape and molded in contact with the fuel rich layer 14.

The ratio of fuel to chlorine producing compounds may be selectively varied in each of the layers 14, 15 to control the rate of burning and the concentration of chlorine gas. Also, the ratio of the volume of the fuel rich layer 14 to the fuel lean layer 15 may be altered to achieve the desired level of heat and chlorine generated. While the optimal ratio of the volume of the fuel rich layer 14 to the fuel lean layer 15 is 1:6, ratios ranging from 1:3 to 1:10 may be utilized.

In both cases the chlorine generating additive may be a metal chloride comprising a metal powder as a fuel. As a fuel, iron, titanium, manganese or similar metallic powders can be used in both the fuel rich layer 14 and fuel lean layer 15. Certain natural silico-aluminum oxides (for example asbestos) or certain oxides (for example manganese oxide, $MnO_2$) catalyze also the oxidation of chlorides produced by the thermal decomposition of chlorates or perchlorates. Consequently, with an appropriate catalyst, chlorine can be produced from two sources: namely by oxidation of chlorides of aluminum, iron, niobium and similar chlorides and in small amounts by thermal decomposition of chlorates or perchlorates of sodium, lithium and potassium. Certain oxides such as cobalt, manganese and iron catalyze the decomposition of chlorates or perchlorates and thus lower the temperature of the decomposition.

The catalyst may be any one selected from the group consisting of copper oxide, nickel oxide, or mixtures thereof.

As a source of hot gaseous oxygen, thermal decomposition of lithium, sodium or potassium chlorates, alkali metal chlorates, and alkali metal perchlorates and mixtures thereof can be used. These salts can be mixed with a fuel to produce oxygen in a continuous way.

The chlorine generating segment may optionally further include a binder to maintain its candle form.

It is intended that the chlorine gas generator, of the present invention would be placed in an enclosed space to be disinfected and an energizing circuit, which may be powered by a battery, (not shown), would be connected to the wires 16. The connection should be of sufficient length to place the operator outside the enclosed space. When the circuit is energized, the current, in the wires 16 will burn the igniter 11, which will initiate a self propagating burn of the ignition segment 12. The burning of the ignition segment 12, together with the heat from the burning, which is retained by the insulation material 17, will cause the exothermic reaction to continue with a burn of the fuel rich layer 14, in self propagating fashion. As the reaction progresses, the build up of heat will allow the fuel lean layer 15 to burn in self propagating fashion as well. The chemical candle 4 will burn completely. As the burning reaches the fuel rich layer 14, chlorine generating compounds present within the fuel rich layer 14 will begin to produce chlorine gas which is vented through the discharge tube 10. The heat generated by the reaction heats the gas, and the attendant pressure which builds in the container 5 forces the gas out through the tube 10. As the burning fuel rich layer 14 ignites the fuel lean layer 15, the greater concentration of chlorine producing compounds, in the fuel lean layer 15 increases the rate of chlorine gas production.

Multiple chlorine gas generators may be used in one location to increase the concentration of chlorine gas, if necessary.

The following are examples of suitable formulations:

1. A suitable ignition segment 12 may have a composition consisting essentially of 35% by weight iron, 13-15% by weight cobalt oxide, about 5% iron oxide, about 3-4% by weight of a binder, and the balance sodium chlorate. This iron rich mixture can easily be ignited by standard commercially available igniters and safely ignites the chlorine producing candle.

2. Three suitable formulations for a fuel rich layer 14 are:

a) A mixture of 1 mole of iron powder, 1 mole of lithium perchlorate $LiClO_4$ and 1 mole of aluminum chloride $AlCl_3$ produces 0.14 mole of chlorine $Cl_2$, 0.02 mole of activated atomic chlorine Cl and 0.28 mole of oxygen gas. The combustion temperature is 1480 K.

b) A mixture of 1 mole of iron powder, 1 mole of lithium perchlorate $LiClO_4$ and 1 mole of niobium chloride $NbCl_5$ produces 0.25 mole of chlorine $Cl_2$, 0.02 mole of atomic chlorine Cl and 0.19 mole of oxygen. The combustion temperature is 1479 K.

c) About 0.5-15% by weight of a metal powder as a fuel consisting of iron, manganese, nickel, cobalt, copper or a mixture thereof; about 0.1-15% by weight of a catalyst selected from the group consisting of copper oxide, nickel oxide, and combinations thereof; about 0.1-5% by weight of an additive for producing chlorine as chlorides of aluminum, iron, tantalum, niobium; from zero to about 5% by weight of a binder; and the remainder of an oxygen source selected from the group consisting of alkali metal chlorates, alkali metal perchlorates, and mixtures thereof.

3. A suitable formulation for a fuel lean layer 15 is:

About 1-10% by weight of iron powder as a fuel; about 0.1-15% by weight of a catalyst selected from the group consisting of copper oxide, nickel oxide, or mixtures thereof; about 0.5-40% by weight of an additive as a chlorine generator; about 1-5% by weight of a binder; and the remainder of an oxygen source selected from the group consisting of alkali metal chlorates, alkali metal perchlorates, or mixtures thereof. The binder is optional to provide a rigid form of the candle, and glass wool or Wollastonite materials may be used. Wollastonite is a common mineral used in refractory ceramics (those ceramics that are resistant to heat) such as refractory tile and as fillers.

In use, the process of ignition and burning, in a self propagating manner, the compounds described above, in an enclosed space produces chlorine gas for the elimination of undesirable organisms. The reaction of producing chlorine is based on oxidation of the chlorine generator (aluminum chloride, iron chloride or niobium chloride) by oxygen gas at higher temperature according to the stoichiometric equations:

$$4AlCl_3 + 3O_2 \rightarrow 2Al_2O_3 + 6Cl_2$$

$$4FeCl_3 + 3O_2 \rightarrow 2Fe_2O_3 + 6Cl_2$$

$$4NbCl_5 + 5O_2 \rightarrow 2Nb_2O_5 + 20Cl_2$$

The process is effective for destroying biological warfare agents, including viruses, such as equine encephalomyelitis; bacteria, such as those which cause plague, anthrax and tularemia; and fungi, such as coccidioidomycosis; as well as toxic products expressed by such microorganisms, for example, the botulism toxin expressed by the common *Clostridium botulinium* bacterium. Furthermore, this invention is useful for sanitizing buildings and other enclosed spaces by killing and removing organisms such as insects, bacteria, virus, dust mites, spiders, silver fish, fungi and toxic molds such as, but not limited to, *aspergillus oryzae, aspergillus terreus, aspergills versicolor, cladosporium hergbarum, stachybotrys chartarum, penicillium aurantio-griseum, pencillium chrsogenum, pencillium glabrum* and *fusarium oxysporum*. Other variations of the apparatus and uses for the disclosed process may be apparent to those skilled in the art and may be practiced without departing from the scope of the invention.

We claim:

1. A chorine gas generator for disinfecting, comprising:

vented container;

a solid chemical candle being disposed within said vented container, said candle comprising an ignition layer and a chlorine generating segment, said chlorine generating segment including metal powder as fuel, an oxygen source including at least one of an alkali metal chlorates and an alkali metal perchlorate, and a metal chloride as a chlorine source; and an igniter igniting the chemical candle from an outside of the container.

2. The chlorine gas generator as in claim 1, wherein said ignition layer further comprises metal powder, cobalt oxide, metal oxide and an alkali metal chlorate.

3. The chlorine gas generator as in claim 1, further comprising an insulating material within the container, which surrounds the chemical candle.

4. The chlorine gas generator as in claim 1, wherein the igniter further comprises a thermal igniter coil connected by wires to the outside of the container.

5. The chlorine gas generator as in claim 1, wherein said chlorine generating segment of the chemical candle is comprised of at least two layers of varying composition such that a first layer, which is substantially adjacent to the ignition layer, is relatively richer in fuel, and a second layer of said at least two layers is disposed at a greater distance from the ignition layer where said second layer is relatively richer in chlorine generating compound compared to said first layer.

6. The chlorine gas generator as in claim 1, where the chlorine generating segment includes a binder.

7. The chlorine gas generator according to claim 1, further comprising a tube structure being partially disposed within said vented container for venting a gas generated by ignition of said solid chemical candle to an environment.

8. The chlorine gas generator according to claim 1, wherein said chlorine generating segment further comprises a catalyst.

9. The chlorine gas generator according to claim 1, wherein said ignition layer contacts said chlorine generating segment.

10. A process for generating chlorine gas, comprising:
   igniting an ignition segment comprising metal power, cobalt oxide, metal oxide and an alkali metal chlorate resulting in products of combustion; and
   containing the products of combustion in a container, which is adjacent to a chlorine generation segment comprising metal chloride as a chlorine source and a metal oxide catalyst for propagation of the products of the combustion to the chlorine generation segment and complete burning thereof.

11. A process of using a chlorine gas generator for sanitizing swimming pools, small water supplies and sewage tanks, comprising
   placing said chlorine gas generator at least substantially near one of a swimming pool, small water supply and sewage tank environment;
   igniting an ignition segment of said chlorine gas generator, said ignition segment comprising metal power, cobalt oxide, metal oxide and an alkali metal chlorate resulting in products of combustion;
   containing said products of combustion in a container portion, which is adjacent to a chlorine generation segment comprising metal chloride as a chlorine source and a metal oxide catalyst;
   propagating the products of the combustion to the chlorine generation segment for ignition of the chlorine generation segment and complete burning thereof for producing a chlorine gas;
   venting said chlorine gas into said one of said swimming pool, small water supply and sewage tank environment for producing a sanitizing effect.

12. A process of using a chlorine gas generator for destroying biological warfare agents, comprising
   placing said chlorine gas generator at least substantially near an environment including biological warfare agents;
   igniting an ignition segment of said chlorine gas generator, said ignition segment comprising metal power, cobalt oxide, metal oxide and an alkali metal chlorate resulting in products of combustion;
   containing said products of combustion in a container portion, which is adjacent to a chlorine generation segment comprising metal chloride as a chlorine source and a metal oxide catalyst;
   propagating the products of the combustion to the chlorine generation segment for ignition of the chlorine generation segment and complete burning thereof for producing a chlorine gas;
   venting said chlorine gas into said environment for producing a destruction effect on said biological warfare agents.

* * * * *